United States Patent
Shapiro et al.

(10) Patent No.: US 6,945,250 B2
(45) Date of Patent: *Sep. 20, 2005

(54) MAGNETIC CONDOM

(76) Inventors: George Shapiro, 25 Old Sprain Rd., Ardsley, NY (US) 10502; Anthony Nigro, 56 Forest Ave., Cortland Manor, NY (US) 10567

( * ) Notice: Subject to any disclaimer, the term of this patent is extended or adjusted under 35 U.S.C. 154(b) by 0 days.

This patent is subject to a terminal disclaimer.

(21) Appl. No.: 10/803,740

(22) Filed: Mar. 18, 2004

(65) Prior Publication Data

US 2004/0206361 A1 Oct. 21, 2004

Related U.S. Application Data

(62) Division of application No. 10/417,274, filed on Apr. 16, 2003, now Pat. No. 6,863,070.

(51) Int. Cl.[7] .................................................. A61F 6/00
(52) U.S. Cl. ...................................... 128/844; 128/918
(58) Field of Search ................................. 128/842, 844, 128/918; 604/327, 346, 349, 355

(56) References Cited

U.S. PATENT DOCUMENTS

| | | | | |
|---|---|---|---|---|
| 1,982,520 A | * | 11/1934 | Stanislaw | 604/353 |
| 5,158,556 A | * | 10/1992 | Starley | 604/351 |
| 5,201,327 A | * | 4/1993 | Johnson | 128/842 |
| 5,314,447 A | * | 5/1994 | Papurt | 128/842 |
| 5,370,131 A | * | 12/1994 | Hess | 128/844 |
| 5,715,839 A | * | 2/1998 | Strauss et al. | 128/842 |
| 6,589,159 B2 | * | 7/2003 | Paturu | 600/15 |

* cited by examiner

*Primary Examiner*—Henry Bennett
*Assistant Examiner*—Camtu Nguyen
(74) *Attorney, Agent, or Firm*—Lackenbach Siegal LLP

(57) ABSTRACT

A condom is provided with magnetic material disposed in a flexible polymeric material condom at the open end of the condom. The magnetic material may be a magnetized ferrometallic split ring in the open end rib or magnetized ferrometallic particulates embedded in the polymeric material adjacent the condom open end. A permanent or rare earth magnet is fixedly disposed in the condom package to provide magnetizing force to the ferrometallic material in of the rolled condom. Alternatively, a permanent or rare earth magnet in a split ring construction may be embedded in the rib formed at the condom open end.

9 Claims, 4 Drawing Sheets

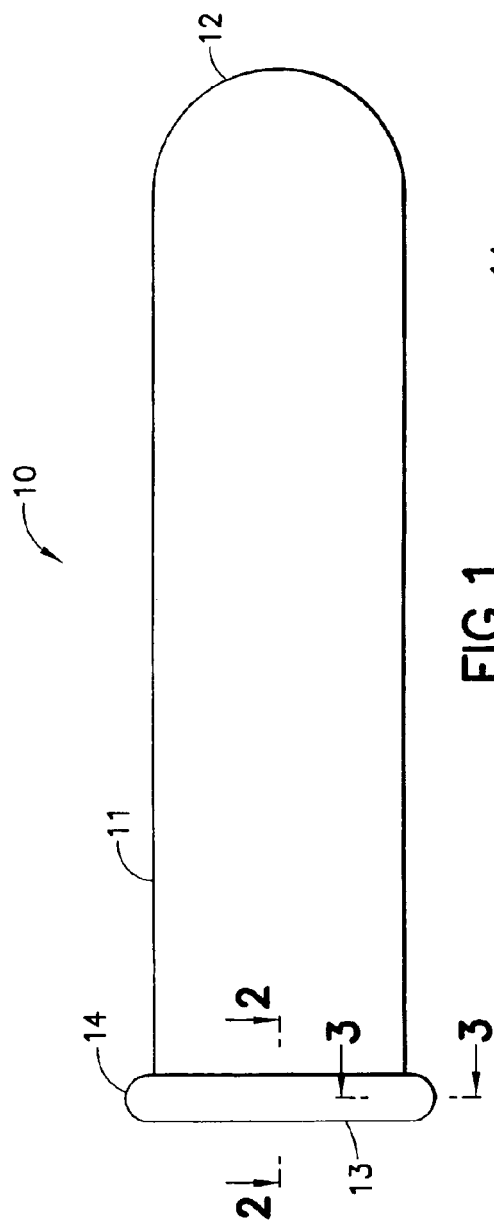
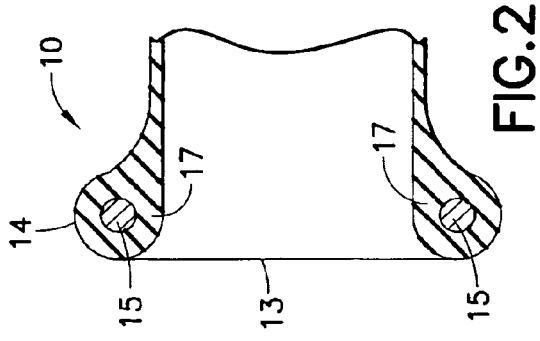
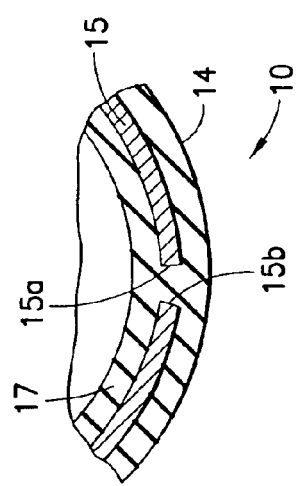

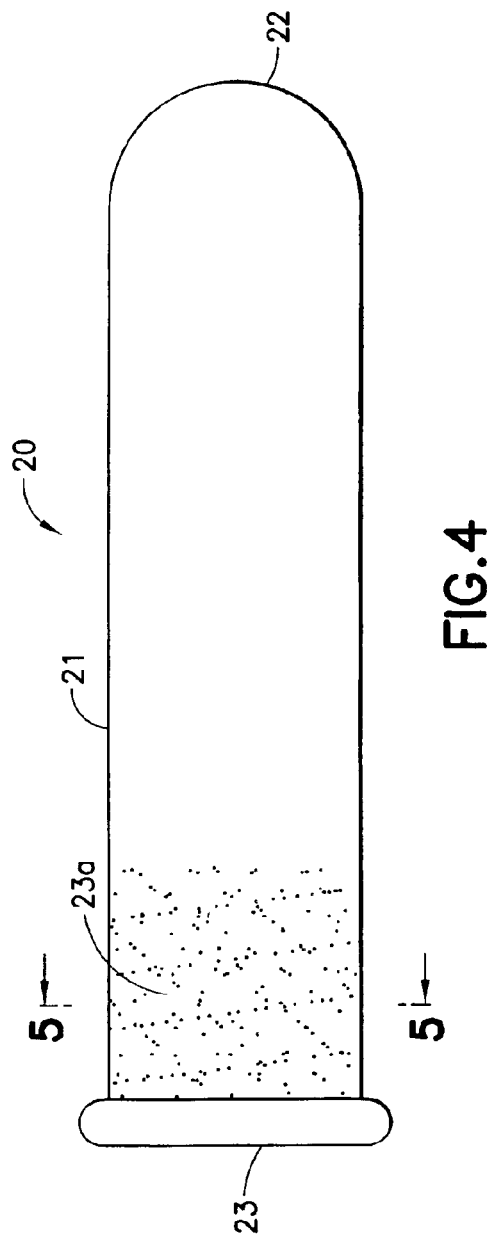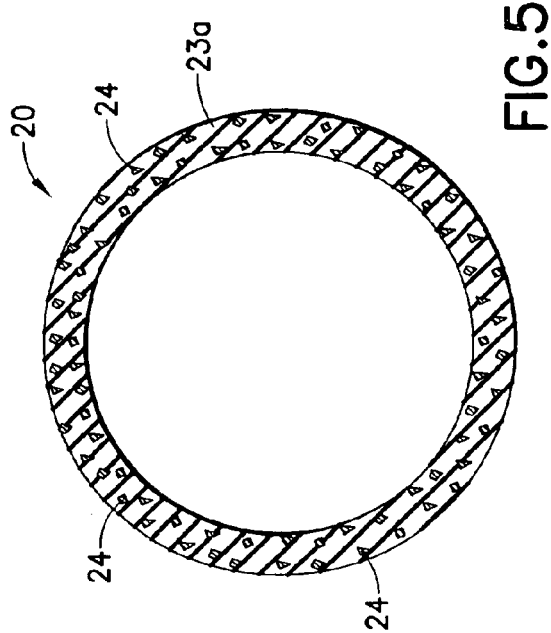

MAGNETIC CONDOM

RELATED PATENT APPLICATIONS

This application is a divisional application of Ser. No. 10/417,274, filed Apr. 16, 2003, now U.S. Pat. No. 6,863,070.

BACKGROUND OF THE INVENTION

1. Field of the Invention

This invention relates to condoms. The invention specifically relates to magnetic condoms.

2. Background and Discussion of the Prior Art

Devices are known that provide static magnetic field therapy in humans. It is believed that static magnetic field therapy may be the result of increased blood flow to the region of the body undergoing a static magnetic field.

A magnetic condom to provide increased blood flood to the penis to achieve erection is disclosed in U.S. Patent Application Publication No. 2002/0151759, dated Oct. 17, 2002, to Paturu. The Paturu published patent application discloses a thick magnetic rubber ring disposed a few millimeters from the closed end of a condom with magnetic particles embedded in the condom at the closed end. The Paturu condom, because of the bulk of the rubber magnet and its disposition, is not practical in design or use. Additionally, the Paturu magnet being disposed at the closed end may not provide the desired level of effective magnetic force and therapy.

It is also known in the condom art to provide electrically conductive particulates such as carbon and silver particulates embedded in the elastic condom sheath for improved electrical communication between the vaginal and penile nerve endings, as disclosed in U.S. Pat. No. 4,971,071 to Johnson.

The condom art desires a magnetic condom that is practical in design, fit, feel and comfort in use.

The condom art also desires an improved condom as aforesaid with increased magnetic field effect.

The condom art also desires an improved condom as aforesaid, which is readily manufactured, so as to be commercially practicable.

SUMMARY OF THE INVENTION

A condom is formed of flexible polymeric sheath material and has magnetic material embedded in the polymeric sheath material adjacent the proximate open end. The magnetic material is disposed at the proximate open end of the condom, and in one preferred aspect the magnetic material is disposed in the condom end rib that forms the open end. The magnetic material may be magnetized ferrometallic particulates, a magnetized ferrometallic ring or a permanent magnet ring disposed in the open end rib. A high energy product rare earth metal magnet is contemplated to provide the requisite magnetizing force.

A packaged condom combines a package with a permanent magnet fixedly attached to the inside of the package, with a condom containing magnetizable ferrometallic material embedded within the condom, so that the magnet provides a magnetic field causing magnetization of the ferrometallic material during extended storage in the package. A rare earth metal pill shaped magnet provides an extended term strong magnetic force to the ferrometallic material embedded in the condom. A rolled condom having ferrometallic material is disposed between two opposed magnets in a package in a further aspect of the packaged condom embodiment.

BRIEF DESCRIPTION OF THE DRAWINGS

FIG. 1 is a side elevational view of a magnetic condom of the present invention;

FIG. 2 is an enlarged sectional view taken along line 2—2 of FIG. 1;

FIG. 3 is an enlarged sectional view taken along line 3—3 of FIG. 1;

FIG. 4 is a side elevational view of a second embodiment of the condom of the present invention;

FIG. 5 is an enlarged sectional view taken along line 5—5 of FIG. 4;

DESCRIPTION OF THE PREFERRED EMBODIMENTS

Figure 6:
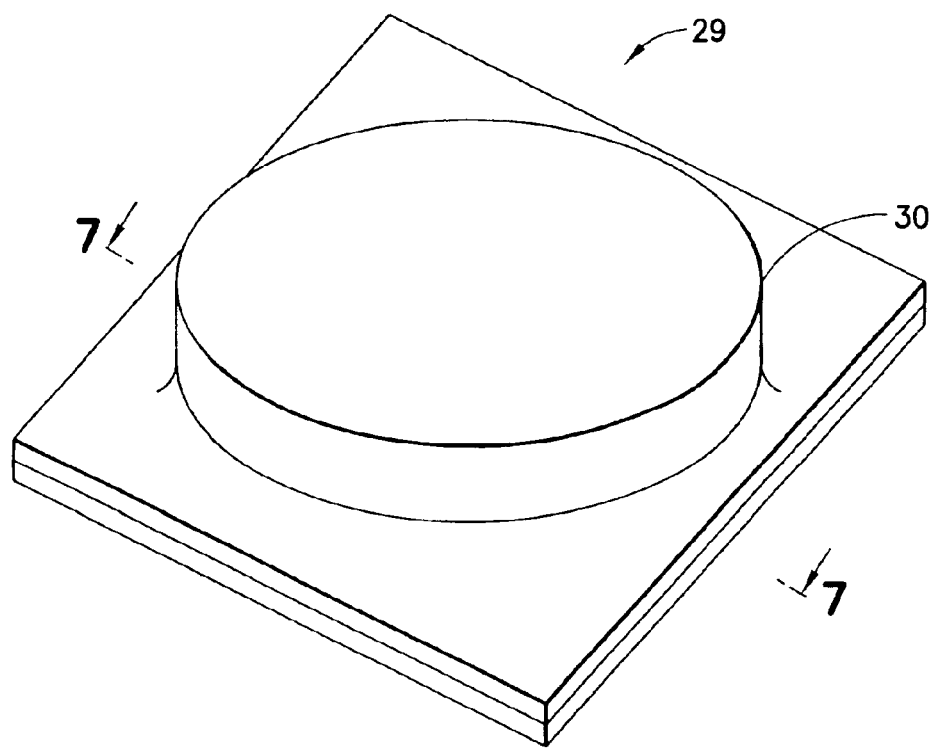
FIG. 6 is a perspective view of the packaged condom embodiment of the present invention.

Referring to FIGS. 1–3, there is shown condom 10 as one embodiment the present invention in the unfurled condition. Condom 10 has a central tubular sheath body portion 11, a distal closed end 12 and a proximate open end 13. A rib 14 is formed at the closed end to provide a seal to prevent semen leakage. A flexible metal ring 15 is embedded in the central portion 16 of rib 14, so that no part of the ring is exposed. The ring 15 is preferably of split ring construction, having opposed split ends 15a and 15b, as best shown in FIG. 3. In this manner of construction, ring 15 flexes and expands with the concomitant flexure and expansion of rib 14.

Ring 15 is formed of magnetic material. In one embodiment, ring 15 is formed of a magnetized ferrometallic material. In a second embodiment, ring 15 is formed of a permanent magnet, particularly including rare earth metal permanent magnet. In this manner of construction, a strong magnetizing force is provided by ring 15 through rib inner wall 17 around the base of the penis. Without wishing to be bound by any theory or mechanism, it is believed that the application of a strong magnetic force or field at the proximate open end of the condom and consequently around the base of the penis provides a particularly effective magnetic field therapy with increased blood flow and circulation to the penis, with concomitantly a maintained erection of the penis.

Referring specifically to FIGS. 4 and 5, there is shown a further embodiment of the invention, namely condom 20. Condom 20 is shown disposed in the unfurled condition. Condom 20 has a central tubular sheath body portion 21, a distal closed end 22 and a proximate open end 23. Rib 24 formed in proximate open end 23 is generally of conventional construction. A plurality of randomly disposed magnetized ferrometallic particulates 24 are embedded in condom 20. Particulates 25 are disposed adjacent the proximate open end 23 (e.g. in area 23a) and extend distally along body portion 21. The particulates 25 are concentrated at or adjacent the open end to provide magnetic therapy to the base of the penis as aforesaid. It is of course understood that the particulates could also be incorporated and embedded along the entire length of the condom if desired. Where the particulates are ferrometallic particulates, a rare earth metal magnet may apply a strong long lasting magnetizing force, as further discussed hereinafter. Condom 20 provides an improved magnetic therapy to the penis, without the user noticing any alteration in the fit or feel of the condom when the penis is erect and particularly so during coitus.

Figure 7:
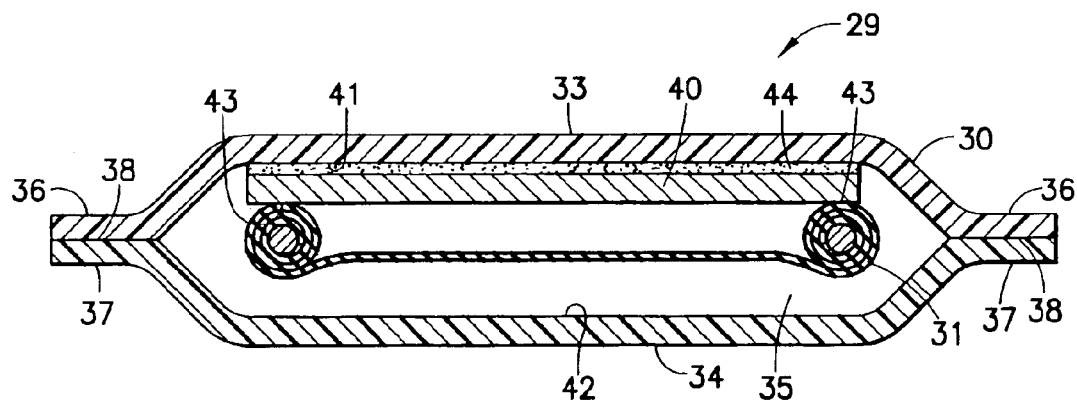
FIG. 7 is a sectional view taken along line 7—7 of FIG. 6.

Referring specifically to FIGS. 6 and 7, there is shown the packaged condom 29 of the present invention. Packaged condom 29, in general terms, includes package 30, rolled condom 31 and at least one permanent magnet 32. Package 30 is formed of flexible non-magnetizable packaging sheet material, such as polymeric material (as shown), or a non-polymeric material (e.g., aluminum, not shown), as well as combinations thereof. Package 30 is formed of generally rectilinear sheet construction having a first sheet 33 and an opposed second sheet 34. Opposed sheets 33 and 34 are sealed to form enclosed pouch 35. Sheets 33 and 34 have respective peripheral edges 36 and 37, which are thermoplastically and/or adhesively sealed as at 38, by means well known in the art.

A permanent magnet 40 is fixedly adhesively disposed on the inside surface 41 of first sheet 33 (FIG. 7). Rolled condom 31 is magnetizely held to magnet 40 and opposed to the inside surface 42 of second sheet 34. Magnet 40 contactingly engages condom 31 at circumferential peripheral area 43. In this manner of construction, magnet 40 or the ferrometallic magnetic material embedded in the condom exerts a magnetic force. Magnet 40 may be disposed in the condom package by other means known in the packaging art.

Figure 8:
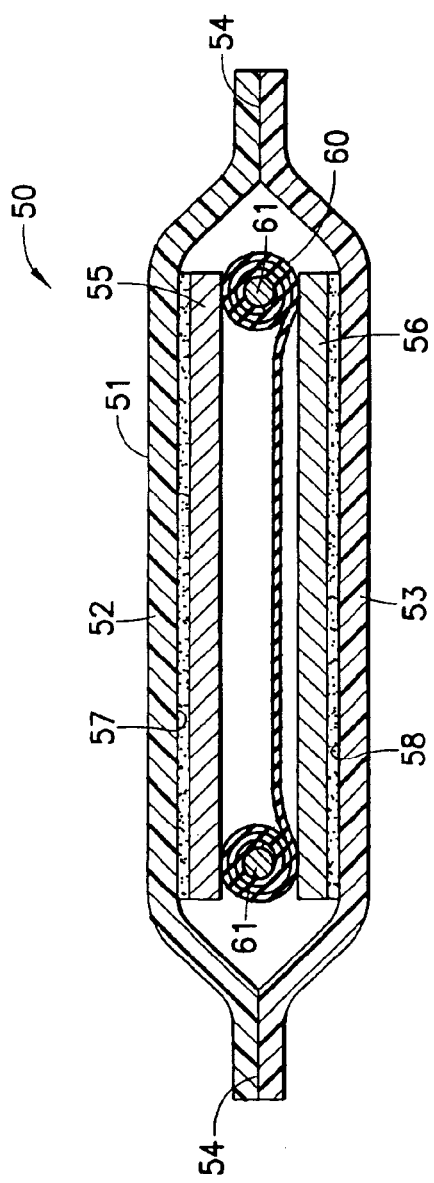
FIG. 8 is a sectional view of a second embodiment of the invention as shown in FIG. 7.

Referring specifically to FIG. 8, there is shown an alternate embodiment of the present invention, packaged condom 50. Packaged condom 50 includes a polymeric package 51 having opposed rectilinear sheets 52 and 53 sealed at the peripheral edges 54 (typical). A pair of opposed permanent magnets 55 and 56 are adhesively fixedly secured by adhesive at 57 and 58 to respective sheets 52 and 53. A rolled condom 60 is held between the magnets. A ferrometallic ring 61, is embedded in the open end rib in the manner as previously discussed. Magnets 55 and 56 are of a shape and pole disposition to provide an increased magnetic force field ferrometallic ring 61.

Figure 9:
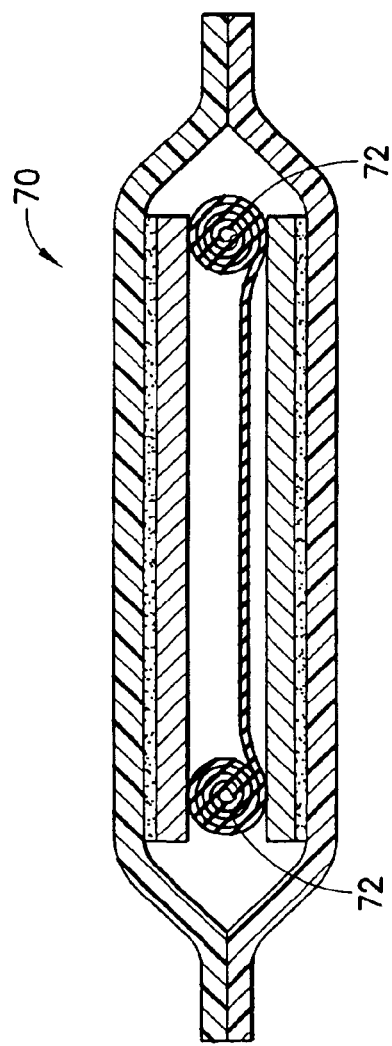
FIG. 9 is a sectional view of a third embodiment of the invention as shown in FIG. 7.

Referring specifically to FIG. 9, there is shown a further embodiment of the invention, packaged condom 70. Packaged condom 70 has a packaging and magnet design construction and arrangement as shown and described with respect to the embodiment 50 of FIG. 8. Packaged condom 70 differs from packaged condom 50 in that condom 71 has ferrometallic particulates 72 embedded in the condom adjacent the open end.

The magnets particularly useful in the present invention are those that provide an enhanced magnetizing field. This is made possible by the use of permanent magnets that have energy products generally equal to at least $7 \times 10^6$ gauss-oersteds, and preferably at least approximately $9 \times 10^6$ gauss-oersteds. Such levels of energy products are obtainable with the classes of materials generally known as neodymium, iron, boron and cobalt rare earth permanent magnets. Such materials are available, for example, from Polymag, Inc. of Bellport, N.Y. and sold under style designations PM70, Poly 10, NDFB30H, NDFB35, NDFB27; and from Hitachi Magnetics Corporation, Division of Hitachi Metals International, Ltd. under the style designations Hicorex 90A, 90B, 96A, 96B, 99A and 99B. The permanent magnets disposed in the packaged condom may preferably be a rare earth metal magnet in pill or ring form.

A thin walled split ring of rare earth metal magnet construction may be embedded in the condom rib, in one further embodiment of the invention. In the latter construction, no magnet is required to be disposed in the package, insofar as the strong force field rare earth magnet ring is embedded in the condom. Differently configured, e.g. tubular or ring magnets of rare earth metal construction are commercially available from Reid Tool Supply Company, at www. REI DTOOL.com/pdf/category/magnets.pdf.

The materials useful for forming condoms of the present invention, include a broad range of elastomeric polymeric materials, such as disclosed in U.S. Pat. No. 5,351,698, to Wheeler et al. which disclosure is incorporated herein by reference thereto. Useful condom sheath materials include elastomeric polymeric materials such as, by way of example, polyurethanes (e.g. polyester based polyurethanes), polyesters, polybutadienes and copolymers thereof, latex, natural rubbers and natural skins.

Generally speaking, the condom of the present invention may be manufactured by means known in the condom manufacturing art. The ferrometallic material, such as particulates, may be embedded in the polymeric sheath material by means disclosed in U.S. Pat. No. 4,971,021 to Johnson, which disclosure is incorporated herein by reference.

The condoms of the invention may comprise a main sheath of generally cylindrical or tubular shape. However, the specific structure of the sheath of the tubular article of the present invention may be widely varied, depending on the mode of application intended, and the specific materials of construction employed.

While the invention has been described with reference to a male condom, one skilled in the art will appreciate it that the invention is equally applicable to use in a female condom. The term "condom" as used hereinbefore and hereinafter contemplates a male or female condom.

While the invention has been described with reference to specific embodiments and features, it will be appreciated that numerous modifications, variations, and embodiments of the invention are possible, and all such apparent variations, modifications, and embodiments are therefore to be regarded as being within the spirit and scope of the invention.

What is claimed is:

1. A condom comprising:
   a flexible polymeric material sheath having a body portion and an open end and a closed end, and rare earth metal magnet material embedded in the condom adjacent the open end, said closed end being free of said magnet material, said magnet material comprises particulates, said particulates being spacedly disposed.

2. The condom of claim 1, said particulates being disposed immediately adjacent the open end.

3. The condom of claim 1, said condom further comprising a rib formed at the open end, said particulates being disposed adjacent said rib.

4. The condom of claim 1, said rare earth metal magnet material comprises at least one selected from cobalt and neodymium.

5. A condom comprising:
   a flexible polymeric material sheath having a body portion, an open end and a closed end, and rare earth metal magnet material embedded in the condom adjacent the open end, said condom further comprises a rib formed at the open end, said magnet material being disposed in said rib, said magnet material comprises a metal ring, said metal ring being split so as to flex with flexure of the rib.

6. The condom of claim 5, said split ring comprising spacedly opposed ends.

7. The condom of claim 5, said closed end being free of magnet material.

8. The condom of claim 5, said rare earth metal magnet material comprises at least one selected from cobalt and neodymium.

9. A condom comprising:

a flexible polymeric sheath having a body portion, an open end and a closed end, a rib formed at the open end, and rare earth material embedded in the condom rib, said rare earth magnet material comprising a ring, said ring being formed so as to flex with flexure of the open end rib.

* * * * *